United States Patent
Tanabe et al.

(10) Patent No.: US 11,191,438 B2
(45) Date of Patent: Dec. 7, 2021

(54) MEASUREMENT APPARATUS AND MEASUREMENT METHOD

(71) Applicant: KYOCERA Corporation, Kyoto (JP)

(72) Inventors: Shigeki Tanabe, Yokohama (JP); Hideki Morita, Yokohama (JP); Isao Masuike, Machida (JP); Shinya Saito, Kawasaki (JP)

(73) Assignee: KYOCERA Corporation, Kyoto (JP)

( * ) Notice: Subject to any disclaimer, the term of this patent is extended or adjusted under 35 U.S.C. 154(b) by 270 days.

(21) Appl. No.: 15/513,451

(22) PCT Filed: Sep. 24, 2015

(86) PCT No.: PCT/JP2015/004843
§ 371 (c)(1),
(2) Date: Mar. 22, 2017

(87) PCT Pub. No.: WO2016/047136
PCT Pub. Date: Mar. 31, 2016

(65) Prior Publication Data
US 2017/0303796 A1    Oct. 26, 2017

(30) Foreign Application Priority Data

Sep. 26, 2014 (JP) .............................. JP2014-197254

(51) Int. Cl.
*A61B 5/024* (2006.01)
*A61B 5/00* (2006.01)
(Continued)

(52) U.S. Cl.
CPC .......... *A61B 5/024* (2013.01); *A61B 5/02416* (2013.01); *A61B 5/6887* (2013.01);
(Continued)

(58) Field of Classification Search
CPC ... A61B 5/024; A61B 5/02416; A61B 5/6887; A61B 5/021; A61B 5/6898;
(Continued)

(56) References Cited

U.S. PATENT DOCUMENTS

| 8,526,998 B2 | 9/2013 | Koide et al. |
| 2003/0009108 A1* | 1/2003 | Kawaguchi .......... A61B 5/0285 |
| | | 600/528 |

(Continued)

FOREIGN PATENT DOCUMENTS

| JP | 2005-270544 A | 10/2005 |
| JP | 2005-270546 A | 10/2005 |

(Continued)

OTHER PUBLICATIONS

International Search Report issued in PCT/JP2015/004843; dated Dec. 1, 2015.
(Continued)

*Primary Examiner* — Chu Chuan Liu
(74) *Attorney, Agent, or Firm* — Studebaker & Brackett PC

(57) ABSTRACT

A measurement apparatus for measuring biological information includes a sensor that executes selectively at least a first detection mode or a second detection mode, and a controller. The controller controls switching to the second detection mode based on output of the sensor while the sensor is in the first detection mode.

9 Claims, 7 Drawing Sheets

(51) Int. Cl.
*H04M 1/21* (2006.01)
*A61B 5/026* (2006.01)
*A61B 5/0205* (2006.01)
*A61B 5/021* (2006.01)
*H04M 1/72454* (2021.01)

(52) U.S. Cl.
CPC ............... *H04M 1/21* (2013.01); *A61B 5/021* (2013.01); *A61B 5/02055* (2013.01); *A61B 5/0261* (2013.01); *A61B 5/6898* (2013.01); *A61B 5/7203* (2013.01); *A61B 5/742* (2013.01); *A61B 5/7405* (2013.01); *A61B 5/7455* (2013.01); *H04M 1/72454* (2021.01); *H04M 2250/12* (2013.01)

(58) Field of Classification Search
CPC ..... A61B 5/7455; A61B 5/742; A61B 5/0261; A61B 5/02055; A61B 5/0202; A61B 5/7405; A61B 5/7203; A61B 5/1455; A61B 5/14551; A61B 5/14552; A61B 5/14532; H04M 1/21
See application file for complete search history.

(56) References Cited

U.S. PATENT DOCUMENTS

| | | | |
|---|---|---|---|
| 2011/0065482 A1 | 3/2011 | Koide et al. | |
| 2011/0201950 A1* | 8/2011 | Poupko | A61B 5/02028 600/506 |
| 2013/0165800 A1* | 6/2013 | Shimizu | A61B 5/022 600/485 |
| 2013/0345569 A1* | 12/2013 | Mestha | A61B 5/0044 600/473 |
| 2015/0011851 A1* | 1/2015 | Mehta | A61B 5/7221 600/324 |
| 2015/0265217 A1* | 9/2015 | Penders | A61B 5/681 600/301 |
| 2016/0374569 A1* | 12/2016 | Breslow | A61B 5/02405 600/301 |

FOREIGN PATENT DOCUMENTS

JP   2012-057962 A   3/2012
WO   2009/139244 A1   11/2009

OTHER PUBLICATIONS

Written Opinion issued in PCT/JP2015/004843; dated Dec. 1, 2015; with English language Concise Explanation.

* cited by examiner

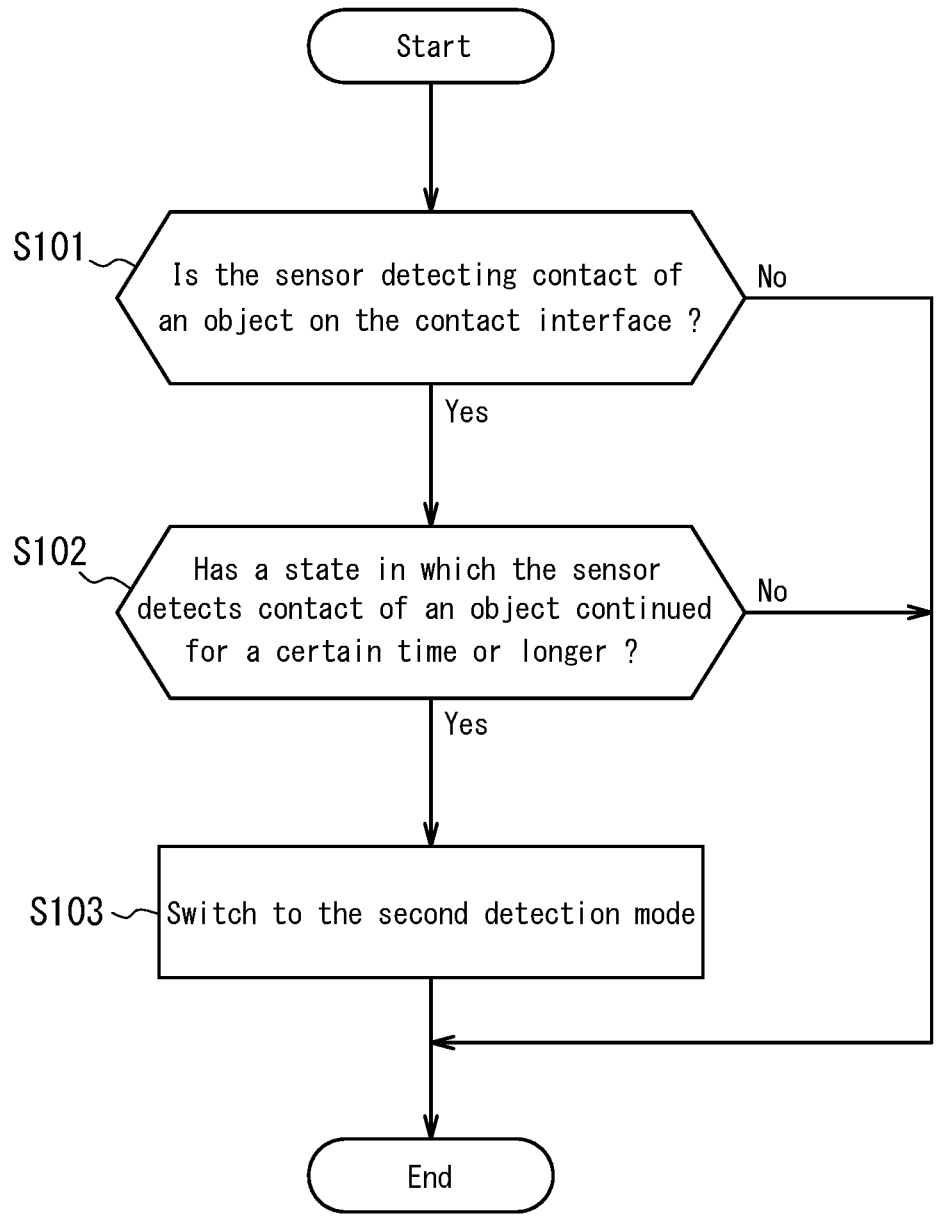

MEASUREMENT APPARATUS AND MEASUREMENT METHOD

CROSS-REFERENCE TO RELATED APPLICATION

This application claims priority to and the benefit of Japanese Patent Application No. 2014-197254 filed Sep. 26, 2014, the entire contents of which are incorporated herein by reference.

TECHNICAL FIELD

The present disclosure relates to a measurement apparatus and a measurement method.

BACKGROUND

Mobile terminals that have a sensor for pulse detection are known.

SUMMARY

A measurement apparatus according to the present disclosure is a measurement apparatus for measuring biological information, the measurement apparatus including:

a sensor configured to execute selectively at least a first detection mode or a second detection mode; and a controller;

such that the controller is configured to control switching to the second detection mode based on output of the sensor while the sensor is in the first detection mode.

The present disclosure may also be implemented as methods substantially corresponding to the above-described measurement apparatuses, and such methods are to be understood as included in the scope of the present disclosure.

For example, a measurement method according to the present disclosure is a measurement method for measuring biological information, the measurement method including:

acquiring, with a controller, output of a sensor that selectively executes at least a first detection mode or a second detection mode by causing the sensor to execute in the first detection mode; and controlling, with the controller, switching to the second detection mode based on the output that is acquired.

BRIEF DESCRIPTION OF THE DRAWINGS

In the accompanying drawings:

FIG. 6 is a flowchart illustrating an example of processing by the controller.

DETAILED DESCRIPTION

A subject (user) can measure the pulse using a mobile terminal that have a sensor for pulse detection. When the subject measures the pulse, the subject first performs an operation to activate the sensor for pulse detection and then contacts a finger to the sensor and begins to measure the pulse.

A measurement apparatus is more user-friendly and useful if the measurement apparatus can be made easier to use when measuring biological information such as pulse, for example by reducing the number of operations the subject performs on the measurement apparatus.

It would therefore be helpful to provide a measurement apparatus and measurement method that are more useful.

The following describes one of the disclosed embodiments in detail with reference to the drawings.

Figure 1:
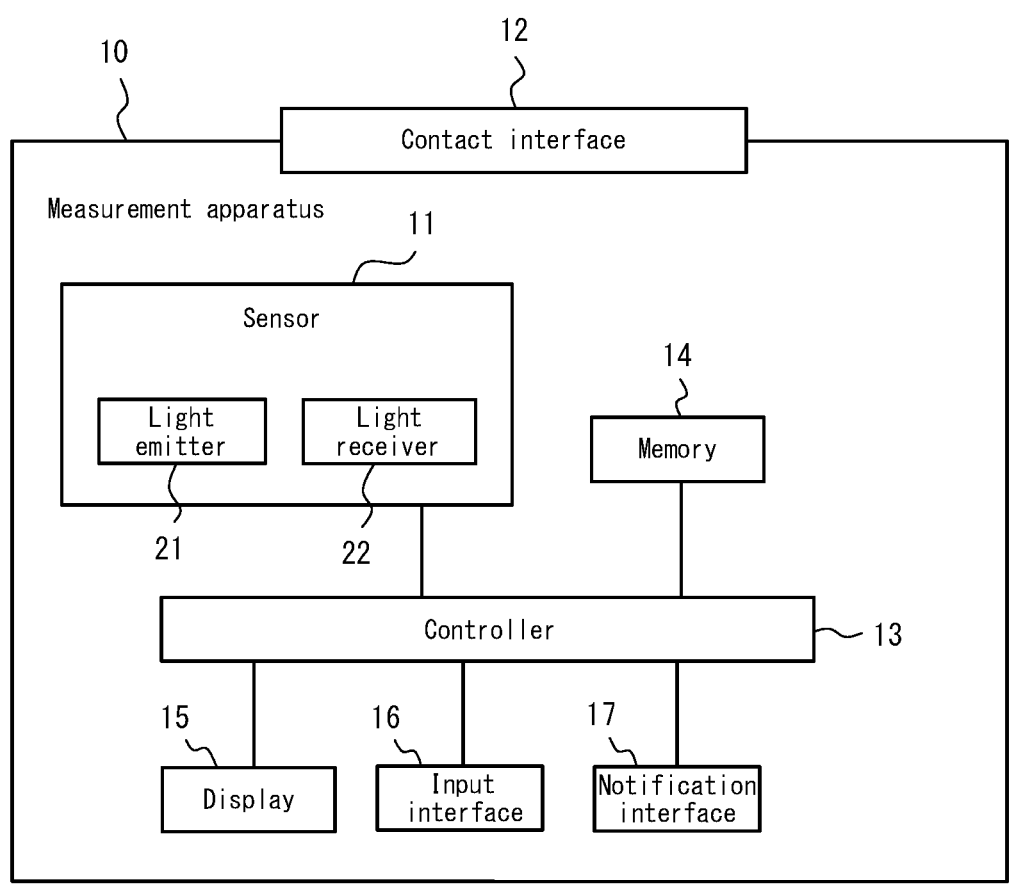
FIG. 1 is a functional block diagram schematically illustrating the structure of a measurement apparatus according to one of the embodiments of the present disclosure.

FIG. 1 is a functional block diagram schematically illustrating the structure of a measurement apparatus according to one of the embodiments of the present disclosure. The measurement apparatus 10 includes a sensor 11, a contact interface 12, a controller 13, a memory 14, a display 15, an input interface 16, and a notification interface 17. The measurement apparatus 10 may, for example, be an electronic device such as a mobile phone or may be an apparatus exclusively for measuring biological information. In addition to being a mobile phone, the electronic device may be any of a variety of other devices, such as a portable music player, a laptop computer, a wristwatch, a tablet, a game device, or the like. In the present disclosure, the measurement apparatus 10 is described as being a mobile phone.

Figure 2:
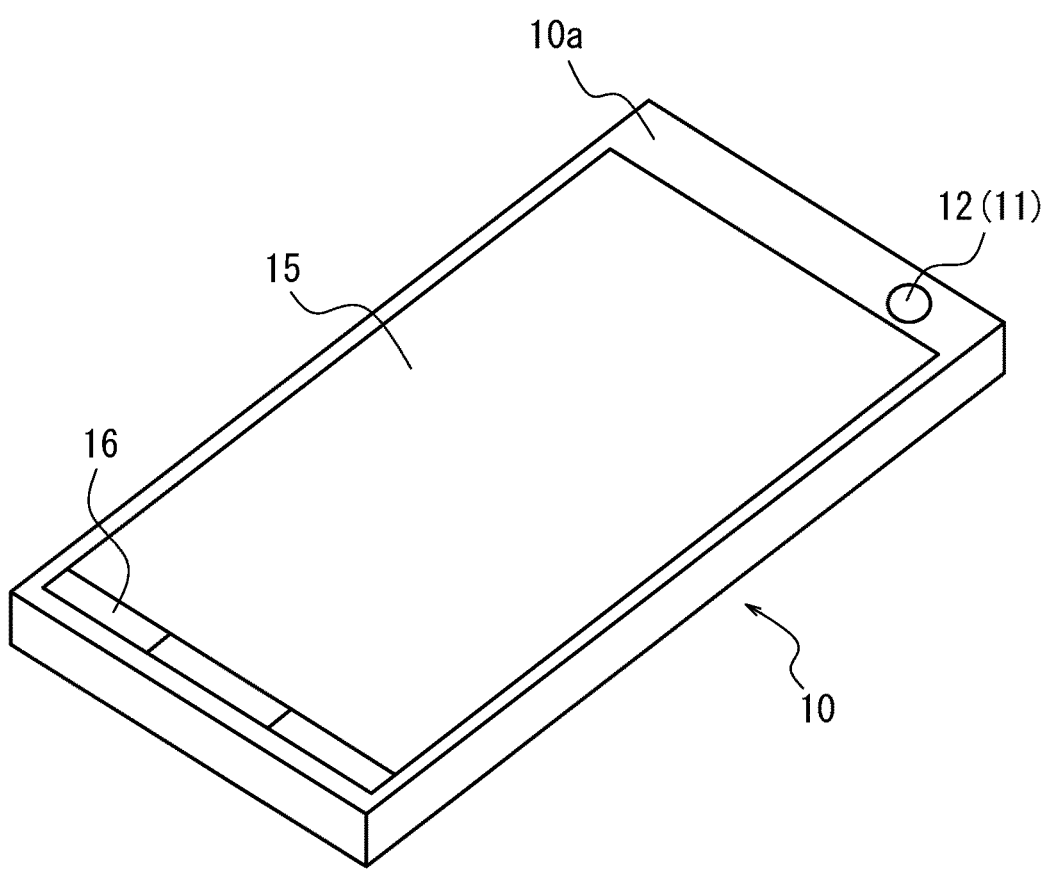
FIG. 2 is an external perspective view of a measurement apparatus according to one of the embodiments of the present disclosure.

FIG. 2 is an external perspective view of the measurement apparatus 10 according to this embodiment. As illustrated in FIG. 2, the measurement apparatus 10 implemented as a mobile phone is provided with the display 15 on the surface 10a side of the mobile phone. The measurement apparatus 10 includes a contact interface 12 near the display 15 on the surface 10a side of the mobile phone. The contact interface 12 is disposed at a position allowing detection of the proximity state between the mobile phone and the subject's face or ear when the user makes a phone call using the mobile phone.

Figure 3:
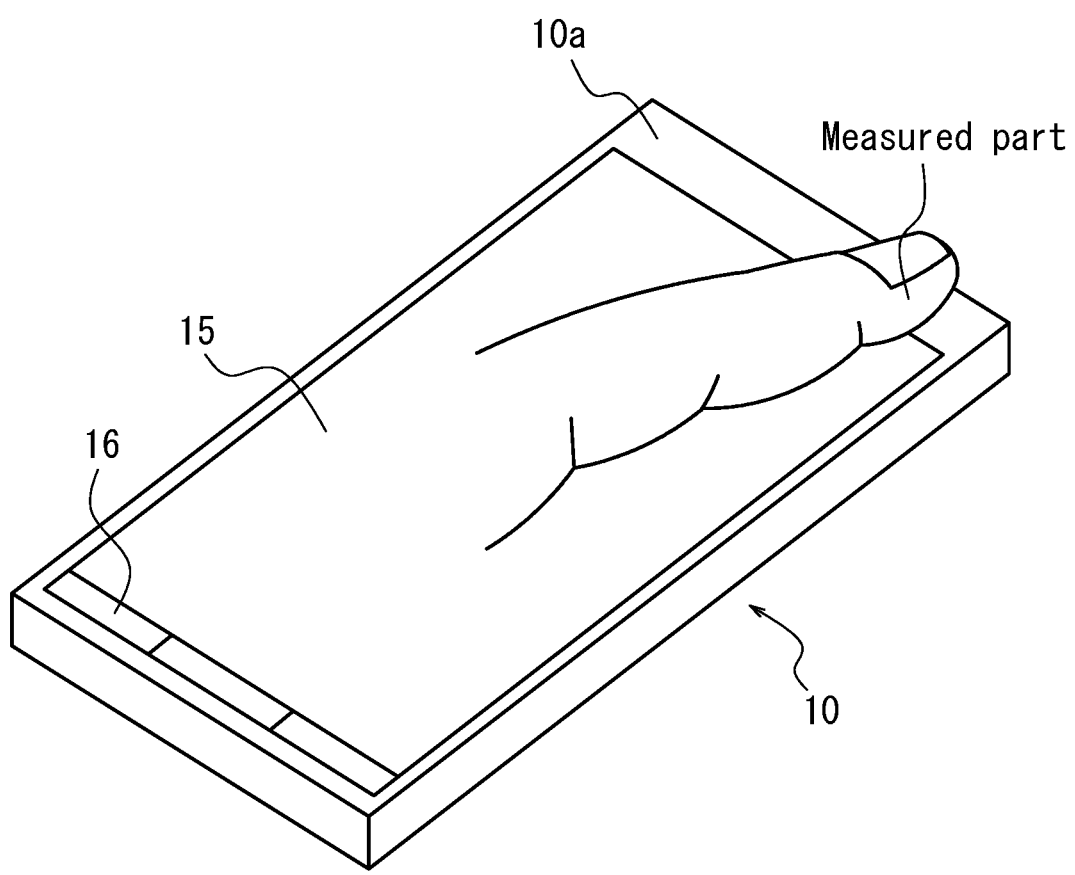
FIG. 3 schematically illustrates the measuring of biological information using the measurement apparatus according to one of the embodiments of the present disclosure.

The measurement apparatus 10 can measure biological information at a measured part in contact with the contact interface 12. FIG. 3 schematically illustrates the subject measuring biological information using the measurement apparatus 10. The subject contacts a fingertip, i.e. the measured part, to the contact interface 12. The measurement apparatus 10 can measure biological information while the measured part is in contact with the contact interface 12.

The biological information measured by the measurement apparatus 10 may be any biological information that can be measured using the sensor 11. In this embodiment, as one example, the measurement apparatus 10 is described below as measuring the subject's pulse. The measurement apparatus 10 may be configured to measure biological information other than pulse, such as the rate of blood flow, blood pressure, or body temperature.

In FIG. 1, based on control by the controller 13, the sensor 11 can execute two detection modes: a first detection mode and a second detection mode. In the first detection mode, the sensor 11 is configured to detect the proximity state of an object, such as the measured part, with respect to the contact interface 12. In the second detection mode, the sensor 11 is configured to detect biological information of the measured part. The sensor 11 is provided with a light emitter 21 and a light receiver 22. Based on control of the light emitter 21 and the light receiver 22 by the controller 13, the sensor 11 implements the first detection mode and the second detection mode.

The light emitter 21 emits measuring light through the contact interface 12 based on control by the controller 13. The measuring light is light that, in the first detection mode, can detect the state related to the degree of proximity of an object such as the measured part (proximity state), and in the second detection mode, can detect biological information of the measured part. In this embodiment, the measuring light is described as being infrared light. The light emitter 21 may, for example, be configured by a Light Emitting Diode (LED) that emits infrared light.

The light receiver 22 receives scattered light that is scattered from the measuring light emitted by the light emitter 21. The light receiver 22 transmits a photoelectric conversion signal of the received scattered light to the controller 13. Based on the intensity of the scattered light received by the light receiver 22 in the first detection mode, the controller 13 determines the proximity state between an object, such as the measured part, and the contact interface 12. Based on the intensity of the scattered light received by the light receiver 22 in the second detection mode, the controller 13 measures biological information. The light receiver 22 may, for example, be configured by a photodiode (PD).

The infrared light emitted onto the biological tissue by the light emitter 21 is absorbed by hemoglobin in the blood. Therefore, as the blood flow is greater, the amount of scattered light received by the light receiver 22 decreases. The amount of blood flowing at the measured part of a blood vessel changes in accordance with heartbeat. Therefore, based on the increase and decrease in the amount of scattered light received by the light receiver 22, the controller 13 can measure the change in the amount of blood at the measured part. Based on this change in the amount of blood, the controller 13 can measure the subject's pulse.

The contact interface 12 is a portion that contacts the measured part, such as a finger, in order for the subject to measure biological information. The contact interface 12 is, for example, configured by a plate-shaped member. The contact interface 12 is configured by a member that is transparent at least with respect to the measuring light from the light emitter 21 and the scattered light from the measured part.

The controller 13 is a processor that, starting with the functional blocks of the measurement apparatus 10, controls and manages the measurement apparatus 10 overall. The controller 13 is configured using a processor such as a Central Processing Unit (CPU) that executes a program prescribing control procedures. Such a program may, for example, be stored in the memory 14, in an external storage medium, or the like.

The controller 13 controls the detection mode of the sensor 11. While causing the sensor 11 to execute the first detection mode, the controller 13 determines whether to cause the sensor 11 to execute the second detection mode based on the detection result of the sensor 11 in the first detection mode. The controller 13 controls the detection mode of the sensor 11 based on the result of the determination. In other words, when determining to cause the sensor 11 to execute the second detection mode, the controller 13 performs control to switch the sensor 11 to the second detection mode. When determining not to cause the sensor 11 to execute the second detection mode, the controller 13 performs control for the sensor 11 to continue the first detection mode.

Upon determining that the proximity state detected by the sensor 11 in the first detection mode is a predetermined proximity state (first proximity state), the controller 13 switches the detection mode of the sensor 11 from the first detection mode to the second detection mode. The first proximity state is, for example, a state in which the measured part is close enough to the contact interface 12 to be in a distance range that allows the sensor 11 to acquire biological information from the measured part. The first proximity state may, for example, be a state in which the measured part is within a predetermined distance range (first distance range) from the contact interface 12 continuously for a certain time or longer. In this embodiment, the first proximity state is described as being a state in which the measured part is in contact with the contact interface 12 continuously for a certain time or longer. In other words, in this embodiment, the controller 13 determines to cause the sensor 11 to execute the second detection mode when the sensor 11 operating in the first detection mode detects, as the proximity state, that the measured part is in contact with the contact interface 12 continuously for a certain time (for example, one second) or longer. The controller 13 then switches the sensor 11 to the second detection mode. Depending on the biological information measured by the measurement apparatus 10 and the configuration of the measurement apparatus 10 for acquiring the biological information, the proximity state need not be a state of contact, and the measurement apparatus 10 may measure biological information in a state in which the measured part is not in contact with the contact interface 12.

In this way, when the sensor 11 detects that the measured part is in contact with the contact interface 12, the controller 13 automatically switches to the second detection mode in which the sensor 11 can detect biological information. As a result, the subject can start measurement of the biological information without performing an operation on the measurement apparatus 10 to start measurement of the biological information.

Upon determining that the proximity state detected by the sensor 11 in the first detection mode is a second proximity state, the controller 13 may turn off display of the display 15. The second proximity state is a state in which an object, such as a portion of the subject's body (for example, the head) is within a second distance range from the contact interface 12 continuously for a certain time or longer. When the subject makes a phone call using the measurement apparatus 10, the sensor 11 in the first detection mode detects that the subject's head is in the second proximity state, and the controller 13 shuts off the display of the display 15. As a result, unnecessary power consumption can be suppressed when the screen is not used during a phone call.

While causing the sensor 11 to execute the second detection mode, the controller 13 determines whether to cause the sensor 11 to execute the first detection mode based on the detection result of the sensor 11 in the second detection mode. The controller 13 controls the detection mode of the sensor 11 based on the result of the determination. In other words, when determining to cause the sensor 11 to execute the first detection mode, the controller 13 performs control to switch the sensor 11 to the first detection mode. When determining not to cause the sensor 11 to execute the first detection mode, the controller 13 performs control for the sensor 11 to continue the second detection mode.

The controller 13 switches the detection mode of the sensor 11 from the second detection mode to the first detection mode when biological information detection output that is output to the controller 13 from the sensor 11 that detected biological information in the second detection mode is not a predetermined biological information detection output. The predetermined biological information detection output is, for example, biological information detection output such that an element included in the detection result is included within a predetermined range. In line with this embodiment, the predetermined biological information detection output is described in detail with reference to FIGS. 4A and 4B.

Figure 4A:
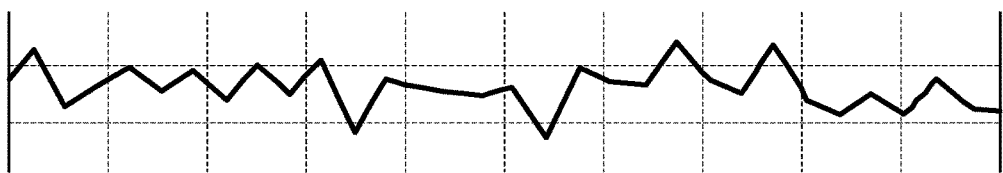
FIGS. 4A and 4B illustrate examples of detection results detected by the sensor in FIG. 1 in the second detection mode.
Figure 4B:
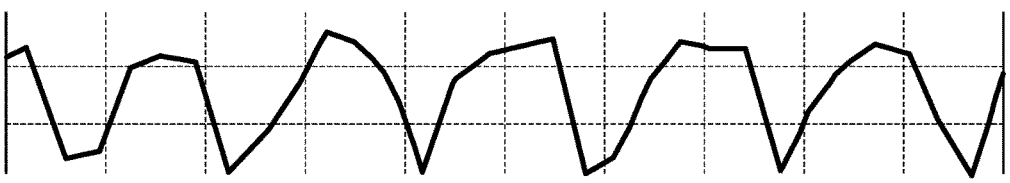

FIGS. 4A and 4B illustrate examples of biological information detected by the sensor 11 in the second detection mode. In this embodiment, in order to measure the pulse with the measurement apparatus 10, the sensor 11 detects pulse wave data of the measured part as the biological information in the second detection mode. The controller 13 determines whether the pulse wave data are valid, i.e. whether an element of the pulse wave data is included in a predetermined range. Here, the controller 13 is described as determining that the pulse wave data in FIG. 4A are not included in a predetermined range (i.e., the biological information detection output from the sensor 11 is not a predetermined biological information detection output) and determining that the pulse wave data in FIG. 4B are included in a predetermined range (i.e., the biological information detection output from the sensor 11 is a predetermined biological information detection output). In the biological information detected by the sensor 11, the variation in the pulse wave data illustrated in FIGS. 4A and 4B is, for example, caused by the contact state such as the contact pressure with which the subject places the measured part in contact.

The controller 13 reduces the noise in the acquired pulse wave data using, for example, a noise removal filter such as a low-pass filter or a digital smoothing filter. In the pulse wave data from which noise was removed, the controller 13 for example detects an inflection point between positive and negative inclination as a peak in the pulse wave data and counts the number of peaks. As an element of the pulse wave data, the controller 13 determines whether the number of peaks in the pulse wave data within a predetermined time is included in a predetermined range. For example, when the pulse wave data detected by the sensor 11 are the data in FIG. 4A, the controller 13 determines the number of peaks of the pulse wave data within a predetermined time for the pulse wave data in FIG. 4A. The controller 13 determines whether the number of peaks is included in a predetermined range. For example, upon determining that the number of peaks is not included in a predetermined range due to being greater than the predetermined range, the controller 13 determines based on the pulse wave data that the biological information detection output from the sensor 11 is not a predetermined biological information detection output. When the pulse wave data is not a predetermined biological information detection output, the controller 13 determines that biological information cannot be measured correctly and switches the sensor 11 to the first detection mode.

When determining that the biological information detection output from the sensor 11 is not a predetermined biological information detection output, the controller 13 need not switch the sensor 11 to the first detection mode immediately. The controller 13 may switch the sensor 11 to the first detection mode when a state in which the biological information detection output from the sensor 11 is not biological information detection output has continued for a certain time (for example, 10 seconds) or longer. As a result, after the subject contacts the measured part to the contact interface 12, if the subject for example is adjusting the contact state, such as the contact pressure of the measured part, in order to cause the measurement apparatus 10 to measure biological information, then time for the adjustment can be guaranteed without the detection mode of the sensor 11 returning immediately to the first detection mode.

When the pulse wave data detected by the sensor 11 are the data in FIG. 4B, then similar to the above-described case, the controller 13 determines whether the number of peaks in the pulse wave data is included in a predetermined range. Upon determining that the number of peaks is within a predetermined range, the controller 13 determines, based on the pulse wave data, that the biological information detection output from the sensor 11 is a predetermined biological information detection output. In this case, the controller 13 causes the sensor 11 to continue operating in the second detection mode and continues detection of pulse wave data.

The element of the pulse wave data that the controller 13 uses to determine, based on the pulse wave data, whether the biological information detection output from the sensor 11 is a predetermined biological information detection output is not limited to the number of peaks. The controller 13 may determine whether the biological information detection output from the sensor 11 is a predetermined biological information output based on another element of the pulse wave data. For example, the controller 13 may use variation in the height of peaks in the pulse wave data as another element of the pulse wave data and determine whether the variation is included in a predetermined range. Variation in the height of peaks may, for example, be prescribed by the standard deviation. In this case, when the standard deviation of the height of peaks is outside a predetermined range, the controller 13 determines, based on the pulse wave data, that the biological information detection output from the sensor 11 is not a predetermined biological information detection output. When the standard deviation of the height of peaks is within a predetermined range, the controller 13 determines that the biological information detection output from the sensor 11 is a predetermined biological information detection output. The controller 13 then controls the detection mode of the sensor 11 based on this determination. The controller 13 may also determine, based on the variation in the interval between peaks as an element of the pulse wave data, whether the biological information detection output from the sensor 11 is a predetermined biological information detection output based on the pulse wave data in a similar way as for the above-described variation in the height of peaks.

In order to determine whether the pulse wave data are valid, the controller 13 may make an overall determination based on a plurality of elements of the pulse wave data.

In this way, when valid biological information detection output is not obtained in the contact interface 12, the controller 13 automatically switches the sensor 11 to the first detection mode. As a result, after the subject finishes measuring biological information and releases the measured part from the contact interface 12, the second detection mode for measuring the biological information can be terminated without the subject performing any operation on the measurement apparatus 10.

The controller 13 drives the light emitter 21 (pulsed light emission) by applying pulsed current to the light emitter 21 and causes the sensor 11 to execute various types of detection. By controlling the pulsed current applied to the light emitter 21, the controller 13 executes control to switch the first detection mode and the second detection mode of the sensor 11. For example by changing the current value, pulse width, and pulse period of the pulsed current and the number of pulses per measurement, the controller 13 can switch the detection mode of the sensor 11. Also, during control to switch the detection mode, the controller 13 may change the measurement interval over which pulsed current is applied. The measurement interval is the interval over which the light emitter 21 applies a plurality of pulses of current.

Figures 5A, 5B:
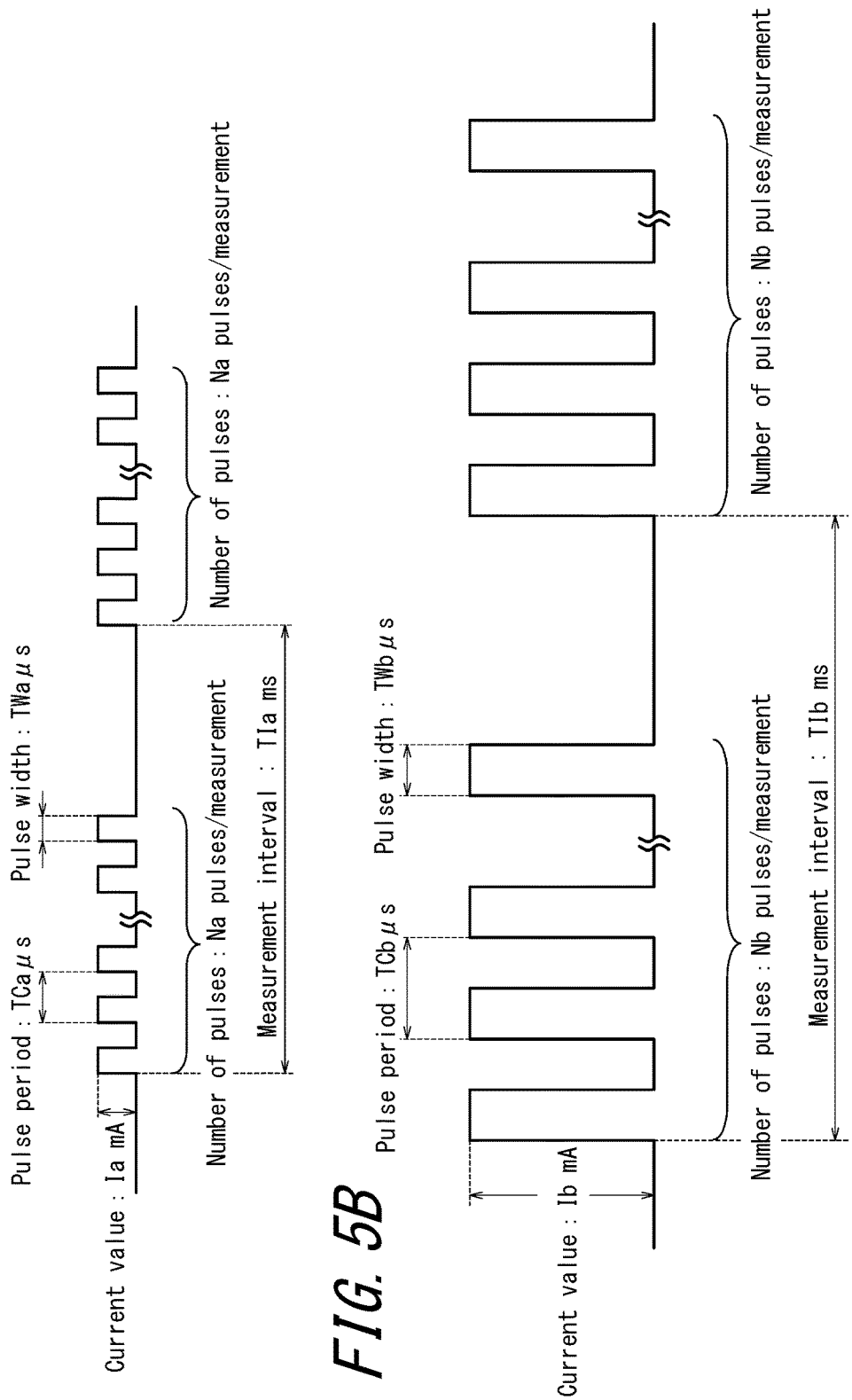
FIGS. 5A and 5B schematically illustrate examples of pulsed current applied by the controller in FIG. 1 to the light emitter.

Here, details on the control by the controller 13 of the sensor 11 in the first detection mode and the second detection mode are provided. FIGS. 5A and 5B schematically illustrate examples of pulsed current applied by the controller 13 to the light emitter 21. The various numerical values related to pulsed current described with reference to FIG. 5, however, are only examples. The controller 13 can apply, to the light emitter 21, pulsed current having any numerical value that allows the sensor 11 to execute the first detection mode and the second detection mode.

FIG. 5A is an example of pulsed current that the controller 13 applies to the light emitter 21 when causing the sensor 11 to execute the first detection mode. As illustrated in FIG. 5A, for each measurement (for example, 0.1 µs to 200000 µs), the controller 13 applies, to the light emitter 21, a pulsed current with a current value of Ia mA, a pulse width of TWa µs, a pulse period of TCa µs, and Na pulses. For example, Ia=0.1 mA to 2000 mA, TWa=0.1 µs to 200000 µs, TCa=0.1 µs to 20000 µs, and the number of pulses Na is appropriately selected from between 1 and 512. The controller 13 applies the pulsed current illustrated in FIG. 5A to the light emitter 21 continuously a plurality of times over a measurement interval TIa ms at which the sensor 11 can detect the proximity state of an object such as the measured part. For example, the measurement interval TIa=0.0001 ms to 200 ms.

FIG. 5B is an example of pulsed current that the controller 13 applies to the light emitter 21 when causing the sensor 11 to execute the second detection mode. As illustrated in FIG. 5B, for each measurement, the controller 13 applies, to the light emitter 21, a pulsed current with a current value of Ib mA, a pulse width of TWb µs, a pulse period of TCb µs, and Nb pulses. For example, Ib=0.1 mA to 2000 mA, TWb=0.1 µs to 200000 µs, TCb=0.1 µs to 200000 µs, and the number of pulses Nb is appropriately selected from between 1 and 512. The controller 13 applies the pulsed current illustrated in FIG. 5B to the light emitter 21 at a measurement interval TIb that allows the sensor 11 to obtain biological information detection output such that the biological information measured by the controller 13 has a predetermined accuracy. As the measurement interval over which pulsed current is repeatedly applied is longer, the number of samples of biological information detection output decreases, making it easy for the accuracy of biological information measured by the controller 13 to degrade. The controller 13 applies pulsed current to the light emitter 21 at a measurement interval such that the measured biological information has accuracy that is reliable as a measurement result. The controller 13 for example applies pulsed current to the light emitter 21 continuously a plurality of times over a measurement interval of TIb=0.0001 ms to 2000 ms.

In the range of pulsed current conditions described with reference to FIG. 5A and FIG. 5B, the controller 13 may more easily consume power in the second detection mode than in the first detection mode. For example, this is the case when, in the second detection mode, the controller 13 applies pulsed current to the light emitter 21 by applying current pulses with a higher current value than in the first detection mode over shorter measurement intervals than in the first detection mode. For example, depending on the combination of pulsed current conditions, such as pulse width, pulse period, and number of pulses, power may be more easily consumed in the second detection mode than in the first detection mode. In this embodiment, when predetermined biological information detection output cannot be obtained in the contact interface 12, the controller 13 automatically switches the sensor 11 to the first detection mode. Therefore, the measurement apparatus 10 can suppress unnecessary power consumption when predetermined biological information detection output cannot be obtained.

When applying pulsed current to the above-described light emitter 21, the controller 13 may apply pulsed current always at a constant pulse period, without providing a measurement interval. Also, the controller 13 may apply current continuously to the above-described light emitter 21, without applying pulsed current.

Other than pulsed current applied to the above-described light emitter 21, the controller 13 may perform control to switch the first and second detection modes by changing the gain, sensitivity, or the like of the light receiver 22. The gain of the light receiver 22 may be changed by, for example, increasing or decreasing the output of an amplifier.

Referring again to FIG. 1, the controller 13 determines whether acquisition of biological information detection output from the sensor 11 in the second detection mode is complete. The controller 13 may, for example, determine that acquisition of the biological information detection output is complete once a predetermined length of time elapses after the sensor 11 starts to acquire the biological information detection output. The controller 13 may also, for example, determine that acquisition of the biological information detection output is complete once biological information detection output sufficient for measuring the biological information has been acquired from the sensor 11.

When determining that acquisition of the biological information detection output is complete, the controller 13 may perform control to switch the detection mode of the sensor 11 to the first detection mode. As a result, after the subject finishes measuring biological information, the second detection mode for measuring the biological information can be terminated without the subject performing any operation on the measurement apparatus 10. The controller 13 may continue the second detection mode of the sensor 11 after determining that acquisition of the biological information detection output is complete. As a result, the subject can continue to measure the pulse. In this embodiment, when determining that acquisition of the biological information detection output is complete, the controller 13 is described below as performing control to switch the detection mode of the sensor 11 to the first detection mode.

Based on the biological information detection output acquired in the second detection mode of the sensor 11, the controller 13 measures biological information. In this embodiment, based on pulse wave data acquired by the sensor 11 in the second detection mode, such as the data illustrated in FIG. 4B, the controller 13 measures the pulse.

When switching the detection mode of the sensor 11, the controller 13 may use the notification interface 17 to notify the subject that the detection mode has been switched. The notification by the notification interface 17 may provide notification only that the detection mode has been switched, or may provide specific notification of whether the detection mode was switched to the first detection mode or the second detection mode.

The notification interface 17 can provide notification for example by a visual method using an image, characters, light emission, or the like; an auditory method using audio or the like; or a combination of these methods. In the case of providing notification with a visual method, the notification interface 17 for example provides notification by displaying images or characters on a display device, such as the display 15. The notification interface 17 may, for example, provide notification by causing an LED or other such light emitting device to emit light. In the case of providing notification with an auditory method, the notification interface 17 for example is a sound generating device, such as a speaker, that provides notification by outputting an alarm sound, audio guidance, or the like. Provision of notification by the notification interface 17 is not limited to a visual or auditory method. Any method recognizable by the subject may be adopted, such as a tactile method based on vibration.

The memory 14 may be configured with a semiconductor memory, a magnetic memory, or the like. The memory 14 stores a variety of information, programs for causing the measurement apparatus 10 to operate, and the like and also functions as a working memory. The memory 14 for example stores a predetermined range (threshold) for each element of pulse wave data. This predetermined range is used by the controller 13 to determine whether the biological information detection output based on pulse wave data acquired in the second detection mode of the sensor 11 is a predetermined biological information detection output.

The display 15 is a display device such as a liquid crystal display, an organic EL display, an inorganic EL display, or the like. The display 15 for example displays the result of the measurement apparatus 10 measuring biological information. By notifying the subject that the controller 13 has switched the detection mode of the sensor 11, the display 15 can also function as the notification interface 17.

The input interface 16 receives operation input from the subject and may be configured, for example, using operation buttons (operation keys). The input interface 16 may be configured as a touch panel, a portion of the display 15 may display the input interface 16 that accepts operation input from the subject, and this portion may accept touch operation input by the subject.

Next, processing executed by the controller 13 is described. FIG. 6 is a flowchart illustrating an example of processing executed by the controller 13. Specifically, FIG. 6 is a flowchart illustrating an example of processing when the controller 13 causes the sensor 11 to operate in the first detection mode.

The controller 13 determines whether the sensor 11 executing the first detection mode has detected contact of an object, such as the measured part, on the contact interface 12 (step S101).

When determining that the sensor 11 has not detected contact of an object on the contact interface 12 (step S101: No), the controller 13 leaves the detection mode of the sensor 11 in the first detection mode and terminates this processing flow. In this case, the controller 13 may restart this processing flow.

When determining that the sensor 11 has detected contact of an object on the contact interface 12 (step S101: Yes), the controller 13 determines whether a state in which the sensor 11 detects contact of the object has continued for a certain time (for example, one second) or longer (step S102).

When determining that the state in which the sensor 11 detects contact of the object has not continued for a certain time or longer (step S102: No), the controller 13 determines that the measured part or another object has temporarily contacted the contact interface 12. The controller 13 then leaves the detection mode of the sensor 11 in the first detection mode and terminates this processing flow. In this case, the controller 13 may restart this processing flow.

When determining that the state in which the sensor 11 detects contact of the object has continued for a certain time or longer (step S102: Yes), the controller 13 determines that the subject may have contacted the measured part to the contact interface 12 and may be attempting to measure biological information. The controller 13 then switches the detection mode of the sensor 11 to the second detection mode (step S103).

Figure 7:
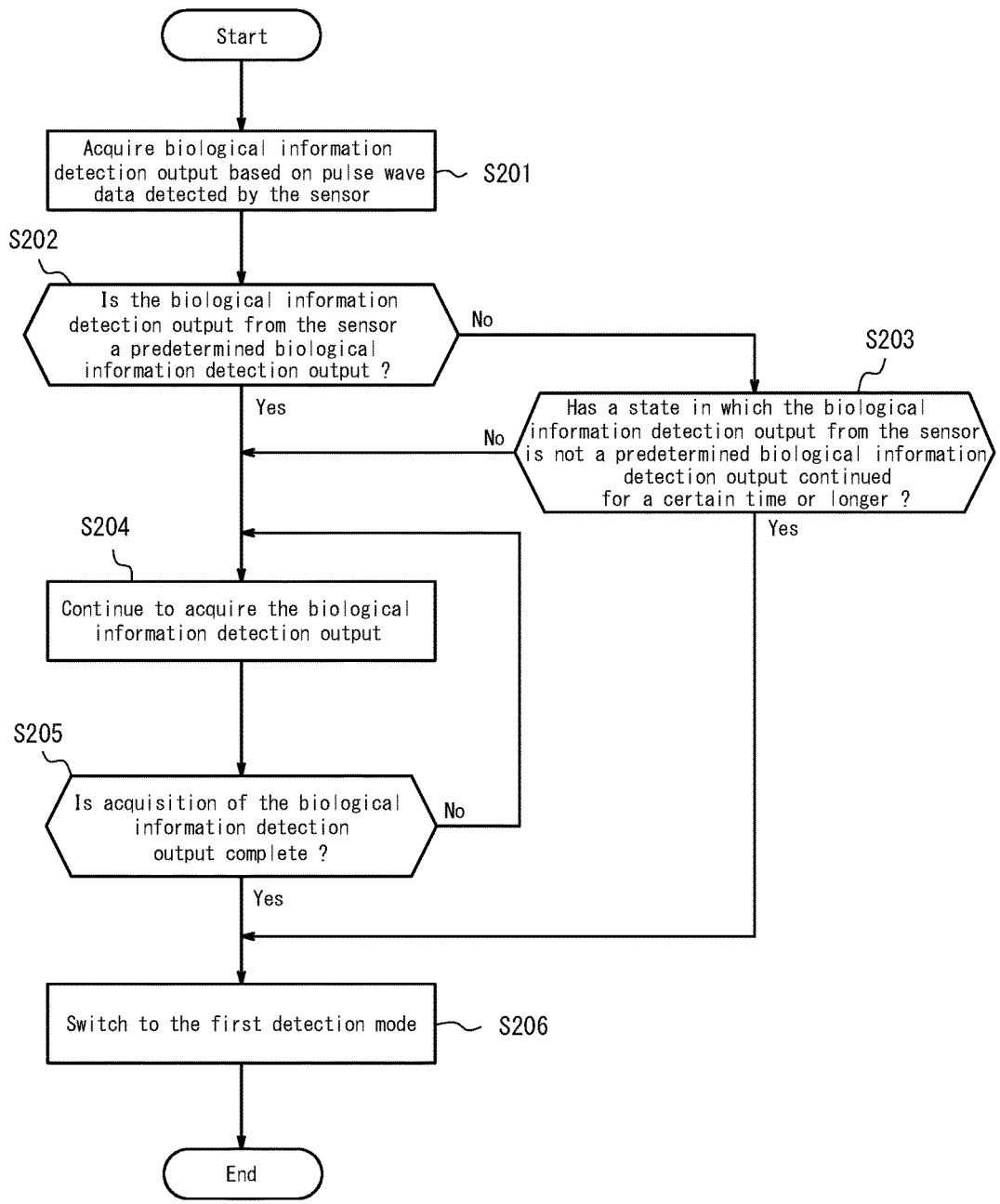
FIG. 7 is a flowchart illustrating an example of processing by the controller.

FIG. 7 is a flowchart illustrating an example of processing executed by the controller 13. Specifically, FIG. 7 is a flowchart illustrating an example of processing when the controller 13 causes the sensor 11 to operate in the second detection mode.

The controller 13 acquires biological information detection output based on pulse wave data detected by the sensor 11 (step S201).

The controller 13 determines whether the biological information detection output from the sensor 11 is a predetermined biological information detection output (step S202).

When determining that the biological information detection output from the sensor 11 is not a predetermined biological information detection output (step S202: No), the controller 13 determines whether a state in which biological information detection output from the sensor 11 is not a predetermined biological information detection output has continued for a certain time (for example, 10 seconds) or longer (step S203).

When determining that a state in which biological information detection output from the sensor 11 is not a predetermined biological information detection output has continued for a certain time or longer (step S203: Yes), the controller 13 determines that biological information detection output cannot be acquired and switches the detection mode of the sensor 11 to the first detection mode (step S206).

When the controller 13 determines that the biological information detection output from the sensor 11 has become a predetermined biological information detection output within a certain time (step S203: No), the processing flow transitions to step S204.

In step S202, when determining that the biological information detection output from the sensor 11 is a predetermined biological information detection output (step S202: Yes), the controller 13 continues to acquire biological information detection output from the sensor 11 (step S204).

Next, the controller 13 determines whether acquisition of biological information detection output is complete because of sufficient biological information detection output for measurement of biological information having been acquired from the sensor 11 (step S205).

When determining that acquisition of biological information detection output is not complete, the controller 13 continues to acquire biological information detection output until acquisition of the biological information detection output is complete (step S204).

When determining that acquisition of the biological information detection output is complete (step S205: Yes), the controller 13 switches the detection mode of the sensor 11 to the first detection mode (step S206). The controller 13 then terminates this processing flow.

In this way, in the measurement apparatus 10 according to this embodiment, the sensor 11 in the first detection mode detects contact of the measured part to the contact interface 12 when the subject contacts the measured part to the contact interface 12. By control of the controller 13, the sensor 11 then executes the second detection mode, and biological information is measured. Upon the subject releasing the measured part from the contact interface 12, the controller 13 determines that biological information cannot be measured based on the detection result of the sensor 11 in the second detection mode. The controller 13 then controls the sensor 11 to be in the first detection mode. In this way, by the subject contacting the measured part to the contact interface 12, the measurement apparatus 10 automatically enters a state in which biological information can be measured, without the subject performing an operation for measurement of the biological information. Therefore, this measurement apparatus is more useful than a known measurement apparatus.

The present disclosure is not limited to the above embodiments, and a variety of modifications and changes are possible. For example, the functions and the like included in the various components and steps may be reordered in any logically consistent way. Furthermore, components or steps may be combined into one or divided.

For example, the sensor 11 in the above embodiment has been described as being configured by an LED that emits infrared light and a PD that receives scattered light. The configuration of the sensor 11 is not, however, limited to this example. The sensor 11 may, for example, be configured by a camera. In this case, the camera detects the proximity state based on the amount of light received by the imaging element configuring the light receiver 22. In other words, when the amount of light received by the imaging element is equal to or less than a predetermined amount of light, the controller 13 determines that the contact interface 12 is covered by an object such as the measured part and switches the camera to the second detection mode. Instead of, or in addition to, the amount of light received by the imaging element, the controller 13 may detect the proximity state based on each RGB component of light received by the imaging element. For example, when the amount of light received by the imaging element is equal to or less than a predetermined amount of light, and the red (R) component of that light is a predetermined ratio or higher than the green (G) component and blue (B) component, then the controller 13 determines that the contact interface 12 is covered by a living organism such as the measured part and switches the camera to the second detection mode.

In the second detection mode, a flash (LED) configuring the light emitter 21 emits visible light on the measured part. The controller 13 determines whether biological information detection output acquired from the camera is a predetermined biological information detection output based on the detection result of visible scattered light received by the imaging element. When determining that the biological information detection output from the camera is a predetermined biological information detection output, the controller 13 continues to acquire biological information detection output from the camera and measures biological information based on the acquired biological information detection output. On the other hand, when determining that biological information detection output from the camera is not a predetermined biological information detection output, the controller 13 switches the camera to the first detection mode.

In the above embodiment, the sensor 11 has been described as capable of executing two detection modes, i.e. the first detection mode and the second detection mode, but the number of detection modes executable by the sensor 11 is not limited to two. The sensor 11 may execute another, additional detection mode. For example, the following describes the case of the sensor 11 being capable of executing a third detection mode.

The third detection mode is used for the controller 13 to determine whether the object contacting the contact interface 12 is part of a living organism, such as the measured part. Upon the sensor 11 in the first detection mode detecting contact of an object on the contact interface 12, the controller 13 for example controls the pulsed current applied to the light emitter 21, thereby switching the sensor 11 to the third detection mode. In the third detection mode, the light emitter 21 emits measuring light that allows a determination of whether the object contacting the contact interface 12 is part of a living organism. Based on the output result of the light receiver 22 in the third detection mode, the controller 13 determines whether the object contacting the contact interface 12 is part of a living organism. For example, if there is periodic variation in the acquired data, the controller 13 determines that the object in contact is part of a living organism.

When determining that the object contacting the contact interface 12 is not part of a living organism, the controller 13 switches the sensor 11 to the first detection mode. Conversely, when determining that the object contacting the contact interface 12 is part of a living organism, controller 13 switches the sensor 11 to the second detection mode. Upon determining that the biological information detection output from the sensor 11 in the second detection mode is a predetermined biological information detection output, the controller 13 continues to acquire biological information detection output from the sensor 11 and measures biological information based on the acquired biological information detection output. Upon determining that biological information detection output from the sensor 11 in the second detection mode is not a predetermined biological information detection output, the controller 13 switches the sensor 11 to the first detection mode or the third detection mode.

If power consumption in the third detection mode is lower than in the second detection mode, then as compared to switching directly from the first detection mode to the second detection mode, the controller 13 can, by switching from the first detection mode to the third detection mode, suppress unnecessary power consumption by the measurement apparatus 10 in the case that the object contacting the contact interface 12 is not part of a living organism.

In the above embodiment, the measured part has been described as a fingertip, but the measured part is not limited to being a fingertip. The measured part may be any site that allows detection of biological information by the sensor 11. When the measurement apparatus 10 measures pulse as in the above embodiment, the measured part is a part where the skin is thin, such as the earlobe, tragus, helix, or the like.

In the above embodiments, the controller 13 provided in the measurement apparatus 10 has been described as generating the biological information based on output of the light receiver 22, but the biological information is not limited to being generated by the controller 13 provided in the measurement apparatus 10. For example, a server that is connected to the measurement apparatus 10 by a network that is wired, wireless, or a combination of both may be provided with a functional component corresponding to the controller 13, and the server that includes this functional component may generate the biological information. In this case, the measurement apparatus 10 acquires the biological information detection output via the sensor 11 in the second detection mode and transmits the acquired biological information detection output to the server via a separately provided communication interface. The server generates the biological information based on the biological information detection output and transmits the generated biological information to the measurement apparatus 10. The user can view the biological information received by the measurement apparatus 10 by displaying the biological information on the display 15. When the server generates biological information in this way, the measurement apparatus 10 can, for example, be reduced in size as compared to when all of the functional components in FIG. 1 are implemented on one measurement apparatus 10.

The invention claimed is:

1. A measurement apparatus for measuring biological information, the measurement apparatus comprising:
   a sensor configured to execute selectively at least a first detection mode or a second detection mode; and
   a controller, wherein
   the controller is configured to control switching to the second detection mode based on output of the sensor while the sensor is in the first detection mode,
   the first detection mode is to detect a proximity state of a measured part, and the second detection mode is to measure biological information including at least one of a pulse, a rate of blood flow, a blood pressure and a body temperature, from the measured part,
   the sensor comprises a light emitter configured to emit measuring light and a light receiver configured to receive scattered light, which is scattered from the measured part and includes a red component, a green component, and a blue component,
   the light emitter emits pulses of the measuring light by applying pulsed current,
   the controller in the first detection mode determines whether an amount of the light received by the light receiver is equal to or less than a predetermined amount of light, and whether a ratio of the red component of the received light is equal to a predetermined ratio or higher than a ratio of the green component and a ratio of the blue component of the received light, to detect the proximity state of the measured part,
   the controller controls, upon detecting the proximity state of the measured part, first switching from the first detection mode to the second detection mode by changing at least one of current value, pulse width, and pulse period of the pulsed current, a number of pulses per measurement, and a measurement interval, to trigger measuring the biological information, the first switching being performed directly in response to a determination that the amount of light received by the light receiver is equal to or less than the predetermined amount of light, and the ratio of the red component of the received light is equal to the predetermined ratio or higher than the ratio of the green component and the ratio of the blue component of the received light,
   the controller in the second detection mode measures the biological information based on biological information detection output from the sensor and determines whether the biological information detection output from the sensor is not a predetermined biological information detection output, and
   the controller controls, upon determining that the biological information detection output from the sensor is not a predetermined biological information detection output, second switching from the second detection mode to the first detection mode.

2. The measurement apparatus according to claim 1, wherein the biological information detection output includes pulse wave data, and
   wherein the controller determines that the biological information detection output from the sensor is not the predetermined biological information detection output when a number of peaks in the pulse wave data is not included in a predetermined range.

3. The measurement apparatus according to claim 1, wherein the biological information detection output includes pulse wave data, and
   wherein the controller determines that the biological information detection output from the sensor is not the predetermined biological information detection output when a variation in heights of peaks in the pulse wave data is not included in a predetermined range.

4. A measurement apparatus for measuring biological information, the measurement apparatus comprising:
   a sensor configured to execute selectively at least a first detection mode or a second detection mode; and
   a controller, wherein
   the controller is configured to control switching to the second detection mode based on output of the sensor while the sensor is in the first detection mode,
   the first detection mode is to detect a proximity state of a measured part, and the second detection mode is to measure biological information including at least one of a pulse, a rate of blood flow, a blood pressure and a body temperature, from the measured part,
   the sensor comprises a light emitter configured to emit measuring light and a light receiver configured to receive scattered light, which is scattered from the measured part and includes a red component, a green component, and a blue component,
   the light emitter emits pulses of the measuring light by applying pulsed current,
   the controller in the first detection mode determines whether an amount of the light received by the light receiver is equal to or less than a predetermined amount of light, and whether a ratio of the red component of the received light is equal to a predetermined ratio or higher than a ratio of the green component and a ratio of the blue component of the received light, to detect the proximity state of the measured part,
   the controller controls, upon detecting the proximity state of the measured part, first switching from the first detection mode to the second detection mode by changing at least one of gain and sensitivity of the light receiver, to trigger measuring the biological information, the first switching being performed directly in response to a determination that the amount of light received by the light receiver is equal to or less than the predetermined amount of light, and the ratio of the red component of the received light is equal to the predetermined ratio or higher than the ratio of the green component and the ratio of the blue component of the received light,
   the controller in the second detection mode measures the biological information based on biological information detection output from the sensor and determines whether the biological information detection output from the sensor is not a predetermined biological information detection output, and
   the controller controls, upon determining that the biological information detection output from the sensor is not a predetermined biological information detection output, second switching from the second detection mode to the first detection mode.

5. The measurement apparatus according to claim 4, wherein the biological information detection output includes pulse wave data, and
wherein the controller determines that the biological information detection output from the sensor is not the predetermined biological information detection output when a number of peaks in the pulse wave data is not included in a predetermined range.

6. The measurement apparatus according to claim 4, wherein the biological information detection output includes pulse wave data, and
wherein the controller determines that the biological information detection output from the sensor is not the predetermined biological information detection output when a variation in heights of peaks in the pulse wave data is not included in a predetermined range.

7. A measurement method for measuring biological information, the measurement method comprising:
acquiring, with a controller, output of a sensor that selectively executes at least a first detection mode or a second detection mode by causing the sensor to execute in the first detection mode; and
controlling, with the controller, switching to the second detection mode based on the output that is acquired, wherein
the first detection mode is to detect a proximity state of a measured part, and the second detection mode is to measure biological information including at least one of a pulse, a rate of blood flow, a blood pressure and a body temperature, from the measured part,
the sensor comprises a light emitter configured to emit measuring light and a light receiver configured to receive scattered light, which is scattered from the measured part and includes a red component, a green component, and a blue component,
the light emitter emits pulses of the measuring light by applying pulsed current,
the controller in the first detection mode determines whether an amount of the light received by the light receiver is equal to or less than a predetermined amount of light, and whether a ratio of the red component of the received light is equal to a predetermined ratio or higher than a ratio of the green component and a ratio of the blue component of the received light, to detect the proximity state of the measured part, to detect the proximity state of the measured part,
the controlling comprises first switching, with the controller, upon detecting the proximity state of the measured part, from the first detection mode to the second detection mode by changing at least one of current value, pulse width, and pulse period of the pulsed current, a number of pulses per measurement, and a measurement interval, to trigger measuring the biological information, the first switching being performed directly in response to a determination that the amount of light received by the light receiver is equal to or less than the predetermined amount of light, and the ratio of the red component of the received light is equal to the predetermined ratio or higher than the ratio of the green component and the ratio of the blue component of the received light, and
the controlling further comprises:
measuring in the second detection mode the biological information based on biological information detection output from the sensor and determining whether the biological information detection output from the sensor is not a predetermined biological information detection output; and
second switching, upon determining that the biological information detection output from the sensor is not a predetermined biological information detection output, from the second detection mode to the first detection mode.

8. The measurement method according to claim 7, wherein the biological information detection output includes pulse wave data, and
wherein the controlling further comprises determining that the biological information detection output from the sensor is not the predetermined biological information detection output when a number of peaks in the pulse wave data is not included in a predetermined range.

9. The measurement method according to claim 7, wherein the biological information detection output includes pulse wave data, and
wherein the controlling further comprises determining that the biological information detection output from the sensor is not the predetermined biological information detection output when a variation in heights of peaks in the pulse wave data is not included in a predetermined range.

* * * * *